United States Patent [19]

Kerkhoffs

[11] 4,277,563
[45] Jul. 7, 1981

[54] PREPARATION OF FRUCTOSE

[75] Inventor: Pieter L. Kerkhoffs, Geleen, Netherlands

[73] Assignee: Stamicarbon, B.V., Geleen, Netherlands

[21] Appl. No.: 95,680

[22] Filed: Nov. 19, 1979

[30] Foreign Application Priority Data

Nov. 18, 1978 [NL] Netherlands .......................... 7811389

[51] Int. Cl.$^3$ .............................................. C12P 19/14
[52] U.S. Cl. ...................................... 435/99; 435/105; 435/276
[58] Field of Search ..................... 435/95, 99, 105, 276

[56] References Cited

FOREIGN PATENT DOCUMENTS 50-160479 12/1975 Japan ........................................ 435/105

OTHER PUBLICATIONS

Methods in Enzymology, vol. 8, pp. 625–627 (1966).

Primary Examiner—Lionel M. Shapiro
Attorney, Agent, or Firm—Cushman, Darby & Cushman

[57] ABSTRACT

Fructose in a purified form is recovered from plant parts containing fructose polymer, such as inulin, by treatment of the mixed plant parts with an aqueous solution of fructose polymer hydrolyzing enzyme, such as inulase, followed by recovering the remaining solid plant parts and recovering fructose crystals from the aqueous solution.

9 Claims, No Drawings

PREPARATION OF FRUCTOSE

Fructose is a natural compound with a greater sweetening power than natural sugar, and can be tolerated better by diabetics.

Various fructose polymers occur in nature, notably inulin and levan. Inulin is contained in various plants, mainly in tubers and roots of plants belonging to the composite family. Levan occurs in places such as grasses and grains and as a product of bacterial polymerization.

The recovery of fructose from inulin by chemical or enzymatic hydrolysis is known. Inulin itself is recovered from plant parts by extraction.

It is an object of the present invention to provide a simpler and more direct process for the preparation of fructose from plants containing a fructose polymer. According to the process of the present invention fructose is obtained by contacting minced vegetable parts containing a fructose polymer with an aqueous medium containing an enzyme that hydrolyses fructose polymers and, after removal of the remaining vegetable matter, isolating the fructose obtained by enzymatic conversion according to conventional procedures.

The advantages of the process according to the present invention are that an extraction step is avoided and that a pure fructose is obtained that can be crystallized more readily than the fructose obtained by chemical hydrolysis. Another important advantage is that the process according to the present invention can be conducted in a very weakly acid to neutral medium. As a result, the formation of by-products, such as the acid-catalyzed formation of fructose dianhydride and the base-catalyzed aldol condensation, both undesirable by-products, is suppressed almost completely. In the conventional inulin extraction with acid and hydrolysis significant amounts of by-product do form.

The recovery of fructose from plant material containing levan is effected by the enzyme levanase; fructose is recovered from plant material containing inulin with the enzyme inulase.

The plant part or parts used as the starting material is preferably one containing inulin, as inulin is contained in considerable amounts in the tubers or roots of plants that are easy to grow. These plants are readily available and provide an economic source of starting material for the process. In many cases the inulin content ranges between 10 and 20% by weight. Some suitable vegetable materials illustrative for use as starting material include dahlia tubers, *Helianthus Tuberosus*, members of the genus Cichoreum, parsnip, fleawort, (*Inula helenium*), costus roots (*Saussurea lappa*) and Jerusalem artichokes. The parts of the plants rich in inulin are minced into a pulpy mass. Equipment already known in the sugar and starch industry may be used for this purpose, such as slicers, cutters and ball mills.

Inulase is the trivial name of (1-2)fructan-fructanohydrolase, enzyme number EC 3.2.1.7. It is a well-known enzyme capable of breaking up (1-2) fructose compounds. Inulase can be obtained from vegetable material, for example from Jerusalem artichokes, but is obtained in practice from cultures of micro-organisms, such as, i.e. *Saccharomyces fragilis, Aspergillus niger,* and *Helminthosporium oryzae*. The enzyme may be used in the crude or pure form or as a cellular mass that exhibits inulase activity. For convenience, in this specification the activity of the enzyme preparations will be expressed in standard units (SU), one SU being the activity required to produce 1 micromole of fructose per minute from inulin. The amount of enzyme used depends upon several factors, i.a., on the inulin content of the vegetable matter, the activity of the enzyme, and the time available for the reaction. In most cases an amount of enzyme preparation corresponding to an activity of between 10 and 6000 SU, and, more in particular, between 100 and 3000 SU, will be used per gram of inulin contained in the vegetable matter.

The temperature and pH in the reaction are preferably chosen such that the enzyme has the optimum activity under the reaction conditions employed. Thus the specific values that are chosen depend on the origin of the enzyme preparation. The pH will generally range between 3.8 and 8.5 and preferably between 4.5 and 6.5. In the preferred range the formation of by-products is negligible. The temperature will generally be between 10° and 90° C. and preferably between 40° and 75° C. The temperature may be varied during the course of the reaction. The reaction is preferably conducted for a time to substantially completely convert all of the inulin present in the plant parts.

The reaction is conveniently conducted in an aqueous medium by mixing the vegetable pulp and the enzyme preparation, if so desired, with addition of more water. Also pH regulators and enzyme activators may be added. The concentration of the reaction mixture will generally range between 10 and 50% by weight of solids. If so desired, the enzyme preparation may be added in portions in the course of the reaction. The reaction may be carried out in a single stirred reactor or in several stirred reactors connected in series. The residence time will be between 1 and 24 hours in most cases.

Upon termination of the reaction, the remaining vegetable matter is separated from the aqueous fructose-containing solution by filtration or centrifugation. The aqueous solution of fructose can be processed further in the usual way to purify and recover the fructose. Any residual enzyme present can be removed by ultrafiltration or treatment with an ion exchanger. The fructose obtained according to the process of the present invention is found to crystallize better than the fructose hydrolyzed and extracted with dilute acid.

The invention will be elucidated with reference to the following examples and are not intended to limit the present invention beyond the scope of the claims following this specification.

EXAMPLE 1

Chicory roots were washed, cut up, freeze-dried and ground. Freeze-drying was effected to enable the material to be stored for several months without degradation and can be omitted in practice. The freeze dried powder (35 g) was suspended in water (300 ml). An aqueous inulase solution (50 g) was added to this suspension, after which the pH of the mixture was adjusted to 5.0 by the addition of acetic acid and the mixture was heated at 50° C. for 24 hours with stirring. The inulase used in this example was a crude preparation of unknown activity.

After treatment for 24 hours the suspension was centrifuged, resulting in 5 grams of solid retained. The solution remaining after centrifugation was stirred with activated carbon (25 g) for 0.5 hour. After the activated carbon had been filtered off, the solution was passed first over a strongly acid ion exchanger (175 ml of Amberlyst-15, of Rhom & Haas) and then over a weakly basic ion exchanger (175 ml of Duolite A-7, of Dow Chemical). The thus treated discolored neutral solution was then evaporated. After addition of seed crystals and crystallization, the resulting solid substance was stirred with ethanol (100 ml) at 5° C. The crystal mass was filtered, washed with cold ethanol and dried. This resulted in 24.5 grams of fructose crystals. No further inulin or fructose could be extracted from the remaining vegetable matter by means of boiling water or dilute hydrochloric acid. This means that the fructose is recovered virtually quantitatively, when some minor product losses during processing are taken into account.

EXAMPLE 2

Freeze-dried ground chicory roots (10 g) with a water content of 1.3% by weight were stirred with water (90 ml) and an aqueous inulase solution (6 g) for 29 hours at a temperature of 55° C. and at a pH of 5.0 which was adjusted by addition of acetic acid. The inulase solution had an activity of 300 SU per gram.

The residual material (1.5 g) was removed by centrifugation. The solution thus obtained was analyzed and contained 7.15 g of fructose and 0.90 g of glucose. The amount of glucose is higher than could be calculated from the hydrolysis of inulin. An explanation is that the enzyme preparation also possesses some invertase activity, so that some hydrolysis of the sucrose that is probably also contained in the roots can occur. However, the small amount of glucose can easily be separated off, as it remains in the mother liquor upon crystallization.

Pure crystalline fructose was recovered from the sugar solution in the manner described in Example 1.

A blank was run by repeating the above process to determine the effect of natural inulase that may be present in the chicory roots, the difference being that water (6 g) was used instead of the inulase solution. The aqueous phase obtained upon centrifugation contained a negligibly small amount of fructose that could not be determined quantitatively. This blank run indicates that the amount of inulase that may be contained in the chicory roots can be neglected and that the addition of inulase according to the process of the present invention is essential in order to produce fructose in any measurable amount.

EXAMPLE 3

Freeze-dried ground roots of belgian endive (25 g) with a water content of 1,5% by weight were treated as in example 1 with 15 g of an aqueous inulase solution (300 SU/g), yielding 3.8 g of residue and an aqueous solution from which 16.8 g of crystalline fructose could be obtained by the process described in example 1.

EXAMPLE 4

Freeze-dried ground dahlia tubers (20 g) with a water content of 1.6% by weight were treated as in example 1 with 13.4 g of aqueous inulase solution (300 SU/g) and 200 ml of water, yielding 15.1 g of crystalline fructose.

What is claimed is:

1. A process for preparing fructose from plant parts containing a fructose polymer, said process consisting essentially of:
   (1) contacting minced plant parts containing a fructose polymer in an aqueous medium with an enzyme that hydrolyzes fructose polymers and hydrolyzing said polymers to produce fructose;
   (2) removing plant parts from the aqueous reaction solution; and
   (3) isolating the fructose so produced from the aqueous reaction solution.
2. The process according to claim 1 wherein said plant parts contain the fructose polymer inulin and are contacted with inulase enzyme in an aqueous medium.
3. The process according to claims 1 or 2 wherein the hydrolysis reaction is conducted at a pH of between about 3.0 and about 8.5.
4. The process according to claim 3 wherein the hydrolysis reaction is conducted at a pH of between 4.5 and 6.5.
5. The process according to claim 1, 2 or 3 wherein the hydrolysis reaction is conducted at a temperature of between about 40° and about 75° C.
6. The process according to claim 2, 3 or 5 wherein the amount of enzyme used per gram of inulin contained in the plant parts corresponds to an inulase activity of between 10 and 6000 SU.
7. The process according to claim 6 wherein the amount of enzyme used corresponds to an activity of between 100 and 3000 SU.
8. The process according to claim 2 wherein any inulase present in the aqueous solution following step (b) is removed by bringing said solution into contact with an enzyme-deactivating ion exchange resin.
9. A process for preparing fructose enzymatically from plant parts containing inulin and optionally other fructose polymers, said process consisting essentially of:
   (a) contacting said plant parts in an aqueous medium at a pH of about 3.0 to about 8.5, a temperature of between about 40° to about 75° C. with an inulase enzyme present in an amount and for a period of time sufficient to hydrolyze substantially all of the inulin and other fructose polymers present in said plant parts; and thereafter
   (b) separating the remaining solid plant parts from the aqueous reaction solution, and
   (c) recovering fructose from the aqueous solution.

* * * * *